(12) United States Patent
Cao

(10) Patent No.: US 6,871,740 B1
(45) Date of Patent: Mar. 29, 2005

(54) SLIT TIP VENTRICULAR CATHETER

(75) Inventor: HongHoa Cao, Austin, TX (US)

(73) Assignee: Codman & Shurtleff, Inc, Raynham, MA (US)

( * ) Notice: Subject to any disclaimer, the term of this patent is extended or adjusted under 35 U.S.C. 154(b) by 0 days.

(21) Appl. No.: 09/578,426

(22) Filed: May 25, 2000

(51) Int. Cl.$^7$ .............................................. B65D 83/10
(52) U.S. Cl. ................... 206/364; 206/438; 604/164.01
(58) Field of Search ................................ 206/363, 364, 206/438, 439; 604/43, 164.09, 247

(56) References Cited

U.S. PATENT DOCUMENTS

| | | | | |
|---|---|---|---|---|
| 3,750,875 A | * | 8/1973 | Juster | 206/364 |
| 5,131,537 A | * | 7/1992 | Gonzalez | 206/364 |
| 5,215,527 A | * | 6/1993 | Beck et al. | 604/164.09 |
| 5,318,517 A | * | 6/1994 | Reiman | 604/43 |
| 5,358,624 A | * | 10/1994 | Roshdy et al. | 206/363 |
| 6,589,212 B1 | * | 7/2003 | Navis | 604/164.01 |

* cited by examiner

Primary Examiner—David T. Fidei

(57) ABSTRACT

A ventricular catheter of the type having a slit in the distal end to permit the passage of a stylet or endoscope is disclosed. The catheter is packaged with a film tab inserted into the slit to prevent the edges of the slit from knitting or adhering to each other upon sterilization or storage.

4 Claims, 2 Drawing Sheets

SLIT TIP VENTRICULAR CATHETER

This invention is directed to an improvement in a ventricular catheter to prevent a slit at the distal end of the catheter from adhering together or knitting during sterilization or storage.

BACKGROUND OF THE INVENTION

Ventricular catheters are widely used in various procedures including the collection of cerebrospinal fluid, introduction of contrast medium or chemotherapy, the measurement of intracranial pressure and the treatment of hydrocephalus. The proper positioning of the catheter in the ventricular system is facilitated by the use of a rigid stylet or the use of an optical endoscope.

The catheters are generally constructed of silicone elastomer tubing and have a series of fluid flow apertures adjacent the distal end and a slit at the distal end. The slit is capable of opening to permit the terminal end of a stylet or optical endoscope to pass through the slit to properly position the catheter. When the catheter is in the desired position in the ventricle, the stylet or optical endoscope can be removed while leaving the catheter in position. These types of catheters are disclosed in U.S. Pat. Nos. 5,437,626; 5,690,117 and 5,738,666, the disclosures of which are incorporated herein by reference.

One of the difficulties in the use of slit catheters is the tendency of the edges of the catheter adjacent the slit be adhered together or knit together during sterilization or storage and close the slit so that a stylet or optical endoscope cannot be passed through the slit to aid in positioning of the catheter.

SUMMARY OF THE INVENTION

The present invention is directed to an improved slit tip ventricular catheter that is constructed and packaged in a manner to prevent the slit tip from knitting or the edges adhering together during sterilization or storage. The present invention accomplishes this desirable result by inserting a thin inert tab into the slit when the catheter manufactured and retaining the tab in the slit until the catheter is used. At the time of use, the tab is removed from the slit and the catheter is used in the normal manner. Ventricular catheters of the present type are usually packaged in a sterile package and are mounted on a paper board insert.

DETAILED DESCRIPTION OF THE INVENTION

Figure 1:
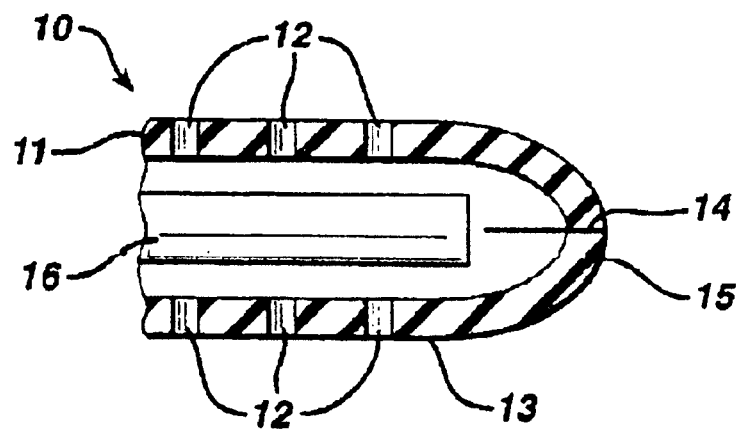
FIG. 1 shows the distal portion of a ventricular catheter.

As shown in FIG. 1, a slit tip ventricular catheter 10 has a tubular body 11 and a number of fluid flow apertures 12 in the distal portion 13 of the tubular body. There is a slit 14 in the distal tip 15 of the catheter.

Figure 2:
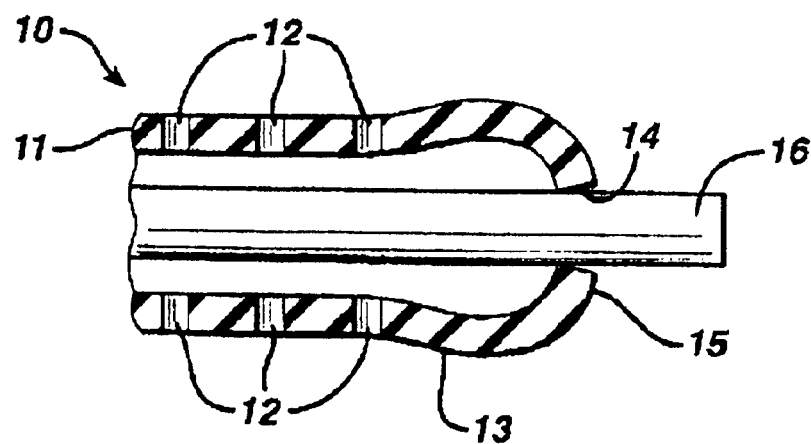
FIG. 2 shows the distal portion of a ventricular catheter with a stylet or endoscope in the distal end.

As shown in FIG. 2, if a stylet or optical endoscope 16 is pushed against the slit 14, the slit will open to allow the stylet or optical endoscope to pass through the distal tip catheter to aid in positioning the catheter.

Ventricular catheters are commonly constructed of a biologically compatible plastic material such as a silicone elastomer, commonly referred to as sliastic. The opposed edges of the slit at the distal end of the catheter are in contact with each other during sterilization and subsequent storage until use. The opposed edges of the slit have a tendency to adhere to each other or knit together. When this knitting occurs, it is difficult and sometimes impossible to force a stylet or optical endoscope through the slit. The catheter must then be removed from the patient and the procedure reinitiated with a different ventricular catheter.

The present invention avoids the aforementioned problem by inserting an inert tab into the slit after the catheter is manufactured and before it is packaged and sterilized. When the catheter is to be used, it is removed from the sterile package and the tab is removed before the catheter placed in use. The tab prevents the opposed edges of the catheter from adhering to each other.

The tab may be made of any inert plastic or paper that can be sterilized and which is compatible with the material from which the catheter is constructed. The tab should be thin enough, about 1 to 3 mils, so that it does not cause a set or gap in the slit when the tab is removed. A thickness of 1 mil or less is preferred. A polyester film having a thickness of 0.92 mil has been found to give excellent results.

Figure 3:
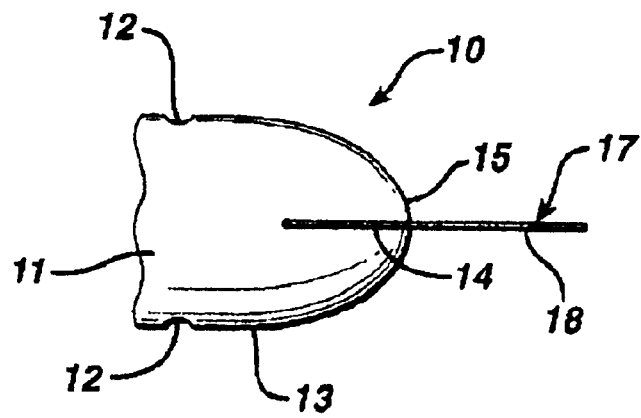
FIG. 3 shows a slit tip catheter of the present invention with a tab positioned in the slit.

As shown in FIG. 3, the tab 17 fits into the slit with an excess of material 18 extending beyond the slit so that the tab can be aseptically removed from the slit in the operating room.

The film tab may be simply inserted into the slit and the catheter packaged for sterilization. However, to prevent the inadvertent removal or loss of the film tab from the slit during processing or storage, a package construction as shown in FIG. 4 may be used.

Figure 4:
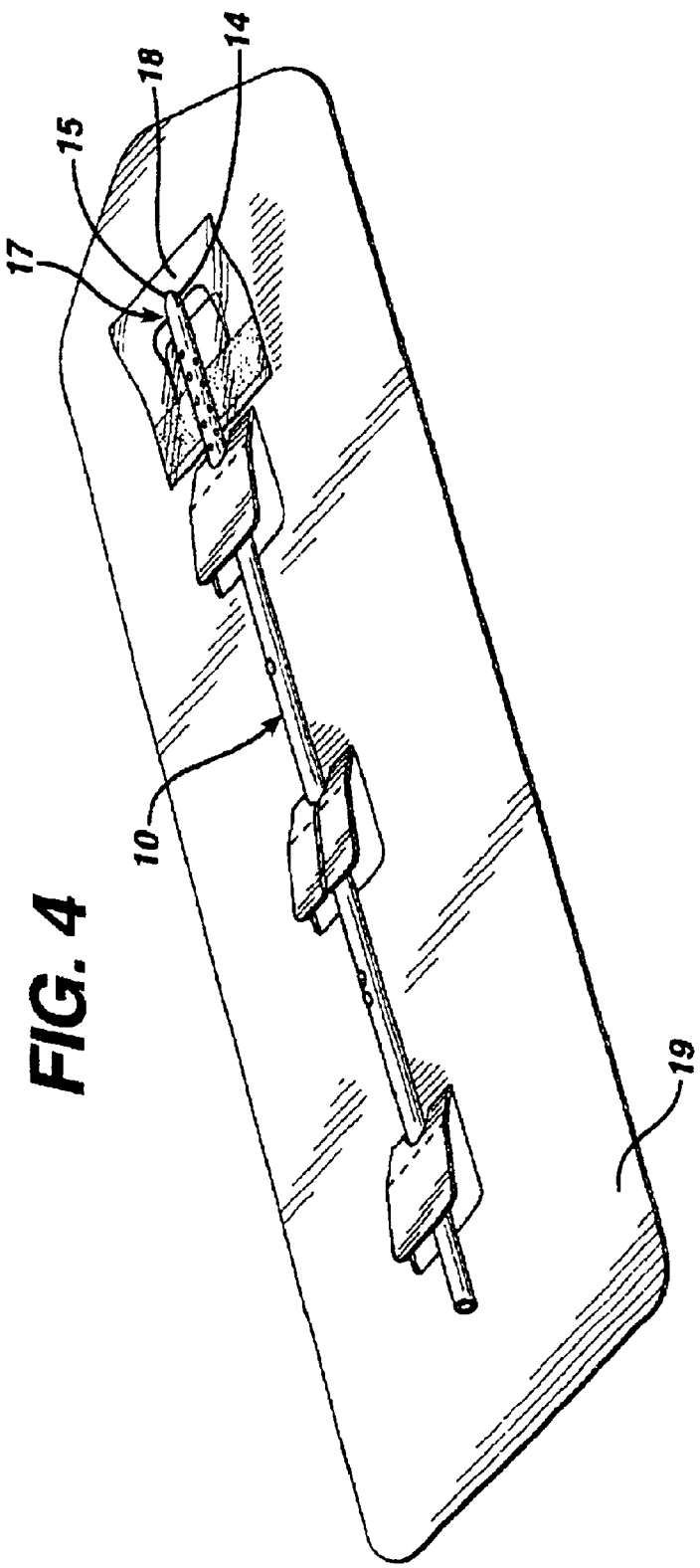
FIG. 4 shows a slit tip catheter mounted on a paper board holder in a sterile package.

As shown in FIG. 4, in the preferred construction of the present invention, the catheter is mounted on a paper board card 19 for packaging. A small rectangular piece of a clear polyester film about 1 inch by ⅞ inch and 0.92 mil thick is secured to the paper board card by a hypoallergenic pressure-sensitive adhesive. Adhesives used are generally hypoallergenic, latex-free, pressure-sensitive adhesives. Adhesives that are preferred are silicone medical adhesives such as SMA available from Dow Corning and MED-1137 available from Nusil Technology.

The film has a free distal end toward the distal end of the catheter and a proximal end which is secured to the paper board holder with the adhesives.

Figure 5:
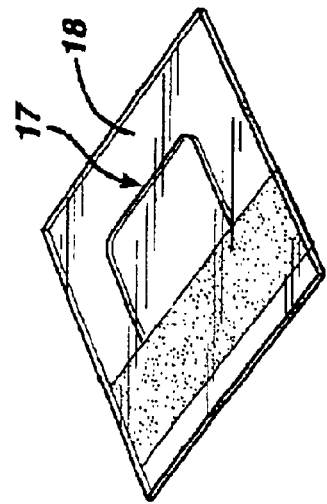
FIG. 5 shows the details of the preferred film tab of the present invention.

As best shown in FIG. 5, there is a C-shape or three sided cut in the middle of the film that provides a flap in the film. A flap 17 is formed at the free end of the film and is inserted into the slit in the distal end of the catheter to prevent knitting. The excess material 18 at the end of the flap allows the catheter to be aseptically removed from the paper board holder 19. The flap 18 can be held and the catheter 10 removed from the holder which separates the film 17 from the slit 14 in the catheter. Securing the film to the paper board card prevents the tab from accidentally falling free of the slit prior to using the catheter. As indicated above, the thinness of the film prevents the slit taking a set and remaining open after the tab is removed.

What is claimed is:

1. A sterilizable ventricular catheter having a proximal end and a distal segment having a plurality of drainage holes and a closed distal end formed with a slit, said slit being movable between a closed configuration and an open configuration, a sterilizable removable film tab inserted into the slit to prevent the edges of the slit from knitting together during sterilization and storage.

2. The catheter of claim 1 in which the distal end of the catheter is removably affixed to a paper board holder and one end of the film tab is adhesively secured to the holder.

3. The catheter of claim 1 in which the film tab has a proximal end and a distal end, said proximal end of the tab being adhesively secured to a holder and the distal end having a flap which is positioned in the slit in the catheter.

4. The catheter of claim 2 in which the film tab is a polyester film having a thickness of about 1 mil.

* * * * *